United States Patent
Green

(10) Patent No.: US 7,668,585 B2
(45) Date of Patent: Feb. 23, 2010

(54) RESPIRATION MONITOR FOR COMPUTED TOMOGRAPHY

(75) Inventor: James W Green, South Russell, OH (US)

(73) Assignee: Koninklijke Philips Electronics N.V., Eindhoven (NL)

(*) Notice: Subject to any disclaimer, the term of this patent is extended or adjusted under 35 U.S.C. 154(b) by 894 days.

(21) Appl. No.: 10/541,705

(22) PCT Filed: Dec. 19, 2003

(86) PCT No.: PCT/IB03/06260

§ 371 (c)(1),
(2), (4) Date: Jul. 8, 2005

(87) PCT Pub. No.: WO2004/062501

PCT Pub. Date: Jul. 29, 2004

(65) Prior Publication Data

US 2006/0074300 A1 Apr. 6, 2006

Related U.S. Application Data

(60) Provisional application No. 60/438,962, filed on Jan. 9, 2003.

(51) Int. Cl.
*A61B 5/05* (2006.01)
*A61B 6/00* (2006.01)
(52) U.S. Cl. .................................. 600/428; 378/8
(58) Field of Classification Search .............. 600/428; 378/8
See application file for complete search history.

(56) References Cited

U.S. PATENT DOCUMENTS

| RE30,101 E | 9/1979 | Kubicek et al. |
|---|---|---|
| 5,067,496 A | 11/1991 | Eisele |
| 5,355,894 A | 10/1994 | Sivard |
| 5,482,042 A | 1/1996 | Fujita |
| 5,485,833 A | 1/1996 | Dietz |
| 5,623,938 A | 4/1997 | Addiss |
| 5,727,554 A | 3/1998 | Kalend et al. |
| 5,913,308 A * | 6/1999 | Forbes et al. ............... 600/513 |
| 6,836,529 B2 * | 12/2004 | Li et al. ........................ 378/8 |
| 2002/0032383 A1 | 3/2002 | Weil et al. |

FOREIGN PATENT DOCUMENTS

EP 0 736 284 A2 3/1996

OTHER PUBLICATIONS

Mori, Masayuki, et al.; Accurate Contiguous Sections without Breath-Holding on Chest CT; 1994; American J. of Roentgenology; 162:5:1057-1062.
Vannier, M. W.; Respiratory Gating by Impedance Plethysmography; 1985; Journal of Nuclear Medicine; 25(10) 1142-1143.

\* cited by examiner

*Primary Examiner*—Eric F Winakur
*Assistant Examiner*—Michael T Rozanski

(57) ABSTRACT

A medical diagnostic imaging system (10) includes a diagnostic imaging scanner (12) that acquires imaging data of a medical imaging patient. A reconstruction processor (46) reconstructs at least a portion of the acquired imaging data into an image representation. A pair of electrodes (30, 32) contact a thoracic region of the patient. An electrical meter (34) measures electrical resistance R(t) or another time-varying electrical parameter (70) across the electrode pair (30, 32) during the acquiring of imaging data. A respiration monitor (36) extracts a time-varying respiration characteristic (90, 98, 110, 120) from the measured time-varying electrical parameter (70) to indicate respiratory cycle phase.

22 Claims, 4 Drawing Sheets

RESPIRATION MONITOR FOR COMPUTED TOMOGRAPHY

CROSS REFERENCE TO RELATED APPLICATIONS

Figure 1:
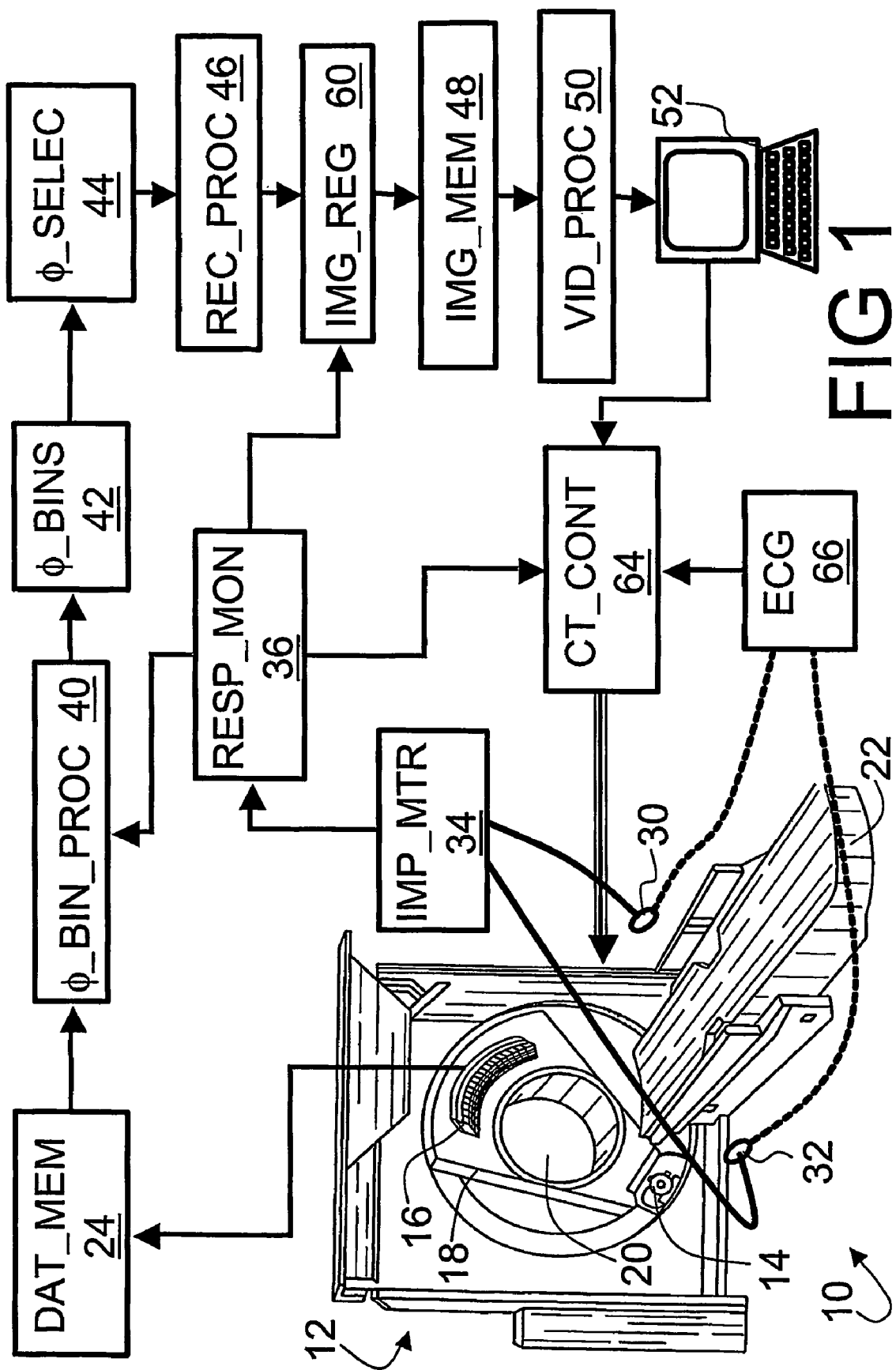

This application claims the benefit of U.S. provisional application Ser. No. 60/438,962 filed Jan. 9, 2003, which is incorporated herein by reference.

The following relates to the diagnostic imaging arts. It finds particular application in respiratory compensated or gated diagnostic imaging, and will be described with particular reference thereto. However, it will also find application in conjunction with various diagnostic imaging modalities, such as computed tomography, single photon emission computed tomography, positron emission tomography, magnetic resonance imaging, and the like.

In situ monitoring of patient respiration during medical diagnostic imaging advantageously facilitates image registration over the respiratory cycle, sorting or binning of acquired imaging data with respect to respiratory state, data filtering based on respiratory state, prospective respiratory gating, radiation dose modulation synchronized with the respiratory cycle, and the like. Respiratory monitoring can also be useful for automating imaging. For example, initiation of imaging can be triggered by detection of the start of a patient breath-hold.

Heretofore, patient respiration has been monitored by electromechanical transducers that monitor chest movement. These electromechanical devices are relatively bulky, can feel uncomfortably restrictive to the patient, and may inhibit chest movement and respiration. In one example, an air filled tube is wrapped around the patient's torso. Inhaling increases pressure in the tube, which is sensed by an associated pressure transducer.

Moreover, electromechanical respiration monitors can interfere with imaging, depending upon the transducer materials and the imaging modality employed. Fitting the patient with an electromechanical transducer is time-consuming and adds complexity to the preparatory phase of the imaging session. In the case of cardiac or other types of imaging in which both the respiratory cycle and the cardiac cycle are monitored, preparation for imaging includes fitting the patient with both the electromechanical respiration monitor and electrodes of an electrocardiograph.

The present invention contemplates an improved apparatus and method that overcomes the aforementioned limitations and others.

According to one aspect, a diagnostic imaging system is disclosed. A diagnostic imaging scanner acquires imaging data of a subject in an examination region. A reconstruction processor reconstructs the acquired imaging data into an image representation. A pair of electrodes are adapted to contact a thoracic region of the subject. An electrical meter measures a time-varying electrical parameter across the electrode pair. A monitor extracts a time-varying respiration characteristic from the measured time-varying electrical parameter.

According to another aspect, a medical diagnostic imaging method is provided. Imaging data of a medical imaging patient is acquired. At least a part of the acquired imaging data is reconstructed into an image representation. A time-varying electrical parameter is measured across an electrodes pair during the acquiring of imaging data. A time-varying respiration characteristic is computed based on the measured time-varying electrical parameter.

One advantage resides in providing respiratory gated medical diagnostic imaging without encumbering the imaging patient with a bulky and uncomfortable electromechanical transducer.

Another advantage resides in providing an electronic signal indicative of aspects of respiratory activity such as inhalation or a breath hold.

Yet another advantage resides in providing respiration information during cardiac computed tomography without contacting the patient with additional probes.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a computed tomography imaging system including in situ respiratory cycle monitoring.

Figure 2:
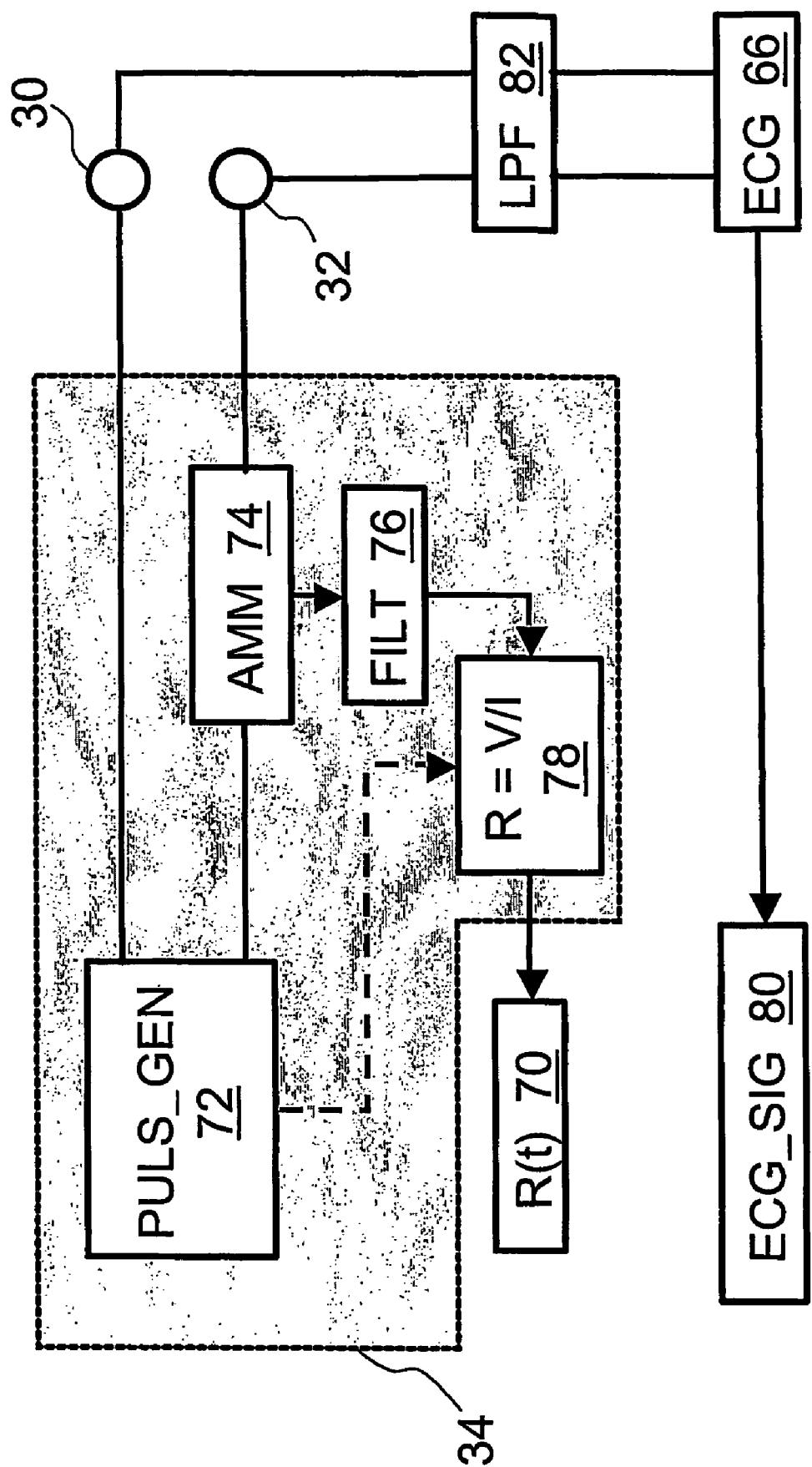

FIG. 2 diagrammatically shows a suitable embodiment of the impedance meter of the computed tomography imaging system of FIG. 1.

Figure 3:
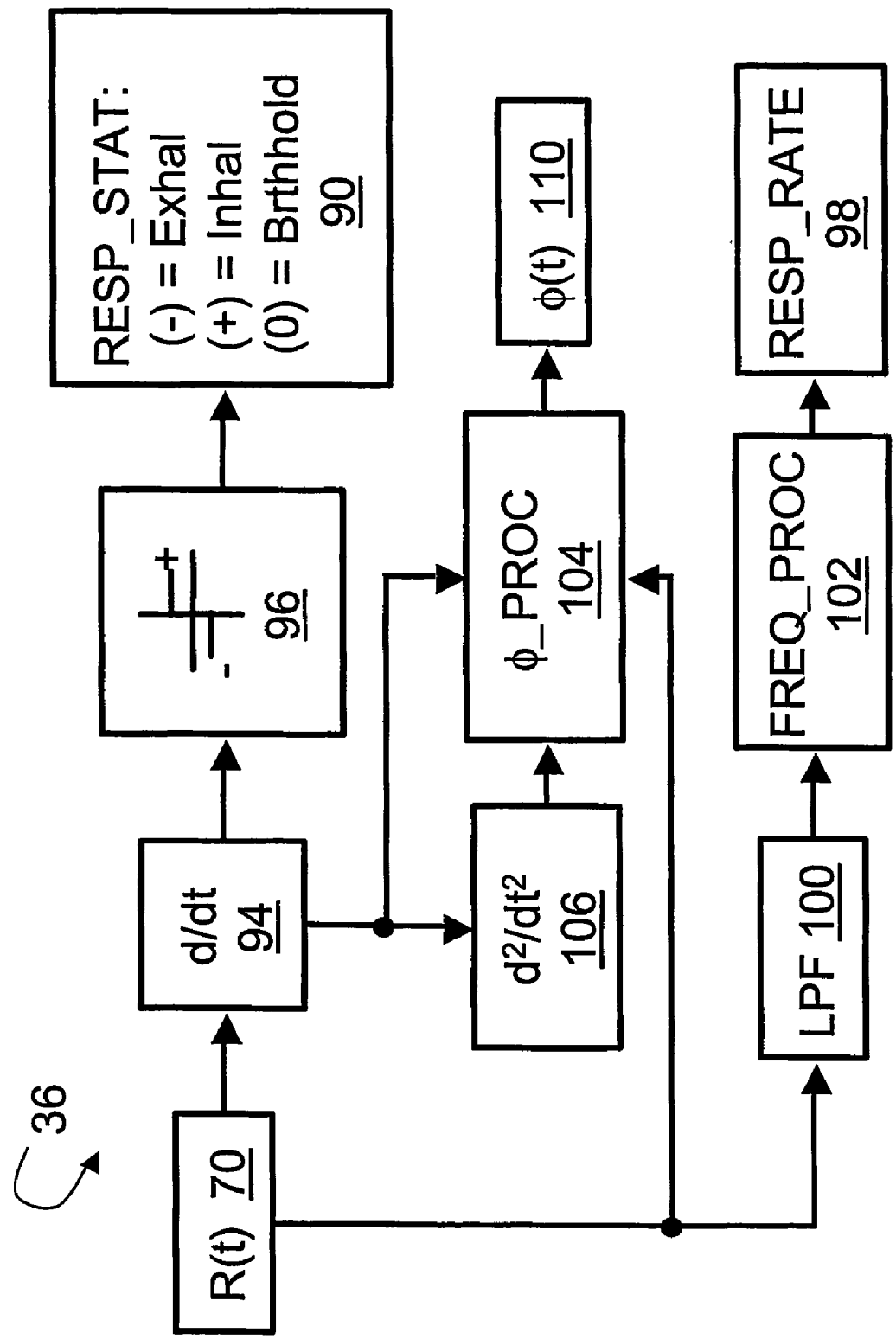

FIG. 3 diagrammatically shows a suitable embodiment of the respiratory monitor of the computed tomography imaging system of FIG. 1.

Figure 4:
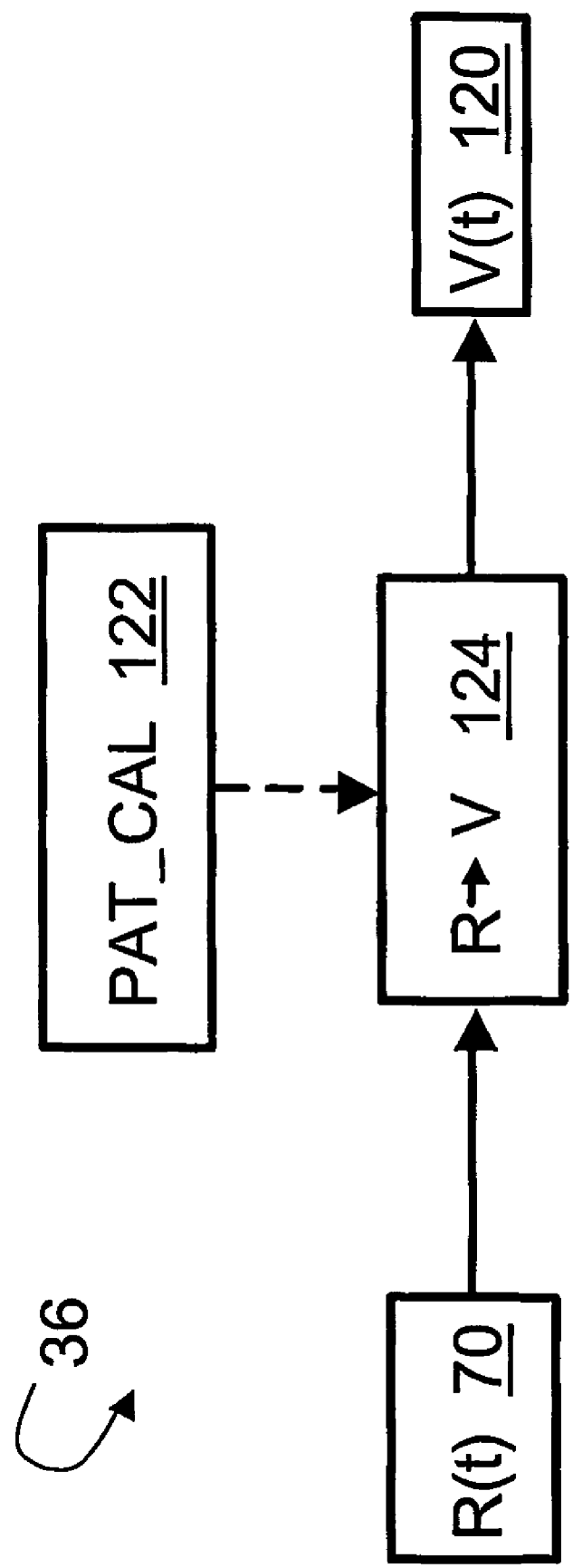

FIG. 4 diagrammatically shows another suitable embodiment of the respiratory monitor of the computed tomography imaging system of FIG. 1.

With reference to FIG. 1, a computed tomography imaging system 10 includes a computed tomography scanner 12. Although the invention is described with exemplary reference to computed tomography, it will be appreciated that the invention will also find application in conjunction with other medical diagnostic imaging systems that employ other imaging modalities such as single photon emission computed tomography, positron emission tomography, magnetic resonance imaging, ultrasound imaging, and the like.

The computed tomography scanner 12 includes an x-ray source 14 and a receiving x-ray detector array 16 oppositely arranged respective to an imaging region 20 defined by a rotating gantry 18. A patient to be imaged is arranged on a subject support 22 and inserted into the imaging region 20. The x-ray source 14 produces a cone-shaped, wedge-shaped, or otherwise-shaped x-ray beam directed into the imaging region 20, where x-rays are partially absorbed by the patient. The absorption-attenuated x-ray intensities are measured at the x-ray detector array 16 after traversing the imaging region 20, and x-ray absorption data generated by the detector is stored in an imaging data memory 24.

Preferably, the gantry 18 rotates continuously during the imaging to acquire projection views over at least a 180° angular span. In helical computed tomography imaging, the subject support 22 advances linearly during the imaging. The combination of linear movement of the subject support 22 and circular rotation of the gantry 18 produces a helical orbiting of the x-ray source 14 about the imaging region 20, during which three-dimensional volumetric imaging data is acquired and stored in the imaging data memory 24.

Prior to the imaging, a pair of electrodes 30, 32 are electrically and mechanically connected to a thoracic region of the patient. Preferably, the electrodes 30, 32 are arranged with a substantial portion of the thoracic region therebetween. The electrodes 30, 32 are suitably made of a material or materials with low x-ray absorption characteristics. Similarly, for other imaging modalities the electrodes are preferably constructed to minimize interference with imaging. For magnetic resonance imaging applications, for example, the electrodes should be made of a non-magnetic material or materials.

The electrodes 30, 32 electrically communicate with an impedance meter 34 that measures an impedance across the electrodes 30, 32. The measured impedance can include resistance, capacitance, inductance, reactance, or a complex impedance combining resistance and reactance. The measured impedance varies with spatial separation of the electrodes 30, 32. This spatial separation changes as the thorax expands and contracts with inhalation and exhalation, and so the measured impedance carries respiratory cycling information. An impedance function is measured, which varies with time as the respiratory cycling progresses.

A respiration monitor 36 receives the measured impedance function and computes one or more respiratory characteristics. For example, a periodicity of the impedance function tracks the respiration rate. A slope of the impedance function relates to respiration state. If the impedance is a resistance, the resistance increases with increasing tidal volume of air in the lungs because the path length between the electrodes 30, 32 increases. Hence, inhalation is indicated by a positive slope of the time-varying resistance function. Exhalation is similarly indicated by a negative slope of the resistance function. A breath-hold or other extended interval between inhalation and exhalation is indicated by a generally horizontal slope. Extrema (i.e., peaks and valleys, or maxima and minima) of the time-varying impedance function indicate transitions between inhalation and exhalation, and provide temporal markers for estimating respiratory cycle phase.

The one or more respiratory characteristics output by the respiration monitor 36 can be used in various ways. For example, in one application a respiratory cycle binning processor 40 sorts acquired projection views by respiratory cycle phase (φ) which is indicated by the respiratory monitor 36. The respiratory cycle binning processor 40 sorts the projection views into respiratory cycle phase bins 42, with each bin storing projection views acquired over a selected respiratory cycle phase interval. To meet data sampling requirements, some data may be from another phase which is similarly configured. A respiratory cycle phase selector 44 selects one or more respiratory phases for reconstruction. A reconstruction processor 46 reconstructs imaging data stored in the selected respiratory cycle phase bins 42 into one or more volumetric image representations that are stored in an image memory 48. By reconstructing data acquired over a limited respiratory cycle phase interval, image motion blurring due to respiration is reduced. A video processor 50 generates a displayable image from the volumetric image representation, such as a maximum intensity projection, an extracted two-dimensional slice, or a three-dimensional rendering, which is displayed on a computer 52 or other user interfacing device.

In another application, the respiratory characteristic is used to identify respiratory activity during imaging data acquisition. An image registration processor 60 relatively spatially registers image representations based on the monitored respiratory activity to correct for respiration-related motion of an imaged organ of interest. For example, portions of the reconstructed image are expanded or contracted to adjust the images to a constant respiratory state. The video processor 50 produces displayable images of the spatially registered image representations, which have reduced respiration-related motion blurring due to the image registration processing.

In yet another application, the respiratory characteristic is used to trigger image data acquisition or to perform prospective respiratory gating of the data acquisition. For example, the respiratory characteristic can be monitored to detect a breath-hold state. When a breath-hold is detected, an imaging sequence supplied to a computed tomography (CT) scanner controller 64 via the user interface 52 is triggered. In response to the triggering, the controller 64 causes the computed tomography scanner 12 to execute the selected imaging sequence. In prospective respiratory gating, the controller 64 initiates intervals of imaging data acquisition during selected respiratory cycle phase intervals indicated by the respiration monitor 36. Dose-modulated imaging synchronized with the respiratory cycle can similarly be performed.

For cardiac computed tomography imaging, an electrocardiograph 66 suitably monitors cardiac cycling simultaneously with monitoring of the respiratory cycle using the electrodes pair 30, 32. In a preferred embodiment, the impedance meter 34 measures a pulse-modulated signal with a pulse frequency substantially higher than the heart rate. Hence, the impedance measurement signal and the electrocardiographic signal are readily decoupled by frequency selective filtering. The electrocardiograph 66 in the illustrated embodiment gates image data acquisition. Alternatively, the electrocardiographic information is conveyed to the binning processor 40 to bin the data based on both cardiac and pulmonary phase.

With reference to FIG. 2, the exemplary impedance meter 34 measures a time-varying resistance R(t) 70. Specifically, a pulse generator 72 produces a voltage pulse train applied across the electrodes pair 30, 32. The pulse train is preferably has a frequency in the tens of kilohertz range, with the precise frequency selected to lie within applicable frequency allocation bands to avoid generating undesirable radio frequency interference. The frequency of the pulse generator 72 is optionally adjustable, in which case the applied frequency can be optimized to maximize the impedance signal. An amplitude of the voltage pulses is typically a few volts or lower. An ammeter 74 measures current at the pulse train frequency. Optionally, a frequency-selective filter 76 removes noise or other interference from the measured current. An impedance calculator 78 computes the resistance by ratioing applied voltage and measured current to compute the time-varying resistance R(t) 70.

Those skilled in the art can readily modify the exemplary impedance meter 34 to suit specific applications or to take advantage of available electronic components. For example, a current pulse train can be sourced, and voltage measured by voltmeter. Other types of impedance such as capacitance, inductance, or complex impedance can be computed by suitably taking into account phase-shifts between the voltage and current pulses or by otherwise combining the voltage and current data. Moreover, a voltage, current, or other electrical parameter can be used to characterize respiration. For a steady-state voltage pulse train, the output of the ammeter 74 carries respiratory information. For respiratory monitoring during magnetic resonance imaging, a low frequency or d.c. voltage or current is preferably applied to obviate radio frequency interference concerns.

When using the voltage pulse train input produced by the pulse generator 72, it will be appreciated that the electrocardiograph 66 can measure an electrocardiographic signal 80 simultaneously with measurement of the time-varying resistance 70 or other time-varying electrical parameter. Using the electrode pair 30, 32 for both respiratory monitoring and cardiac monitoring advantageously reduces imaging delays and simplifies patient preparation, and further benefits the patient by reducing a total number of contacting probes. To remove the high-frequency signal components produced by the pulse generator 72, a lowpass filter 82 is suitably applied prior to electrocardiographic measurement. Although a separate filtering component 82 is shown in FIG. 2, the filter is optionally omitted if a frequency response of the electrocardiograph 66 is such that the electrocardiograph 66 does not respond to signal components at the pulse train frequency.

With reference to FIG. 3, an exemplary embodiment of the respiration monitor 36 outputs a respiration state 90 which classifies the patient as being in one of an exhalation state, an inhalation state, and a breath-hold or transitional respiratory state. A first derivative processor 94 computes a first derivative of the time-varying resistance 70 using an analog differentiator circuit, numerical differentiation, analytic differentiation of a fitted curve or fitted spline segments, or the like. A threshold processor 96 classifies the first derivative signal as one of positive, negative, or substantially zero. It will be recognized that a positive first derivative of the measured resistance 70 corresponds to an increasing time-varying resistance, which in turn corresponds to an increasing resistance path length that occurs during inhalation chest expansion. Similarly, a negative first derivative of the measured resistance 70 corresponds to a decreasing time-varying resistance, a decreasing path length, and hence exhalation. A substantially zero first derivative of the measured resistance 70 corresponds to a constant thoracic volume, which typically indicates an intentional breath-hold by the patient or a fully inhaled or fully exhaled state.

With continuing reference to FIG. 3, the respiration monitor 36 also preferably measures a respiration rate 98. The respiration rate is relatively low frequency, typically around 12 breaths per minute (~0.2 Hz). In one suitable measurement approach a low pass filter 100, such as a filter with a cutoff frequency $f_c$~0.5 Hz, filters out higher frequency components of the time-varying resistance R(t) 70. A frequency processor 102 determines a temporal frequency of the filtered signal corresponding to the respiration rate 98 using a fast Fourier transform (FFT) analysis, peak detection and counting, or the like.

Other respiratory parameters can similarly be estimated from the time-varying resistance R(t) 70. For example, a respiratory cycle phase processor 104 estimates a respiratory cycle phase $\phi(t)$ 110 based on the time-varying resistance R(t) 70 and/or time-varying functions extracted therefrom such as the first derivative generated by the first derivative processor 94 or a second derivative generated by a second derivative processor 106. To reduce computational complexity, it is typically advantageous to differentiate the output of the first derivative processor 94 to obtain the second derivative, as shown in FIG. 3. However, a method that computes the second derivative directly from the time-varying resistance 70 can also be employed. The respiratory cycle phase $\phi(t)$ 110 is suitably estimated by the respiratory cycle phase processor 104 by curve-fitting the time-varying resistance R(t) 70 and/or derivatives thereof with a suitable respiratory cycle model. Alternatively, the respiratory cycle phase processor 104 can locate critical points (such as maxima, minima, or inflection points) of the time-varying resistance R(t) 70 and/or derivatives thereof that correspond to certain respiratory cycle phases such as transitions from inhalation to exhalation, transitions from exhalation to inhalation, and the like.

With reference to FIG. 4, another exemplary embodiment of the respiration monitor 36 outputs quantitative values for tidal volume V(t) 120 of air in the lungs. Specifically, a patient calibration 122 that correlates tidal volume with resistance between the electrodes 30, 32 is obtained prior to tomographic imaging, for example by measuring resistance values across the electrodes 30, 32 during quantitative spirometric measurement of tidal volumes. Using the patient calibration 122, the time-varying resistance R(t) 70 is processed by a tidal volume transform processor 124 to convert the resistance R(t) 70 to quantitative values of tidal volume V(t) 120.

It will be appreciated that components of the respiration monitor of FIGS. 3 and 5 are readily combinable. Moreover, other respiration characteristics besides the exemplary respiration state, respiration rate, respiration cycle phase, and tidal volume characteristics can be computed based on the time-varying resistance or other time-varying electrical parameter 70. Again, the respiration rate can be fit to a model and used to predict future respiratory cycles.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A diagnostic imaging system including:
   a diagnostic imaging scanner that acquires imaging data of a subject in an examination region;
   a reconstruction processor that reconstructs the acquired imaging data into an image representation;
   a pair of electrodes adapted to externally contact a thoracic region of the subject;
   an electrical meter that measures a time-varying electrical parameter across the electrode pair by applying a voltage or current pulse train having a frequency substantially higher than the heart rate across the pair of electrodes;
   a monitor that extracts a time-varying respiration characteristic from the measured time-varying electrical parameter, the monitor including a differentiator that computes a time derivative of the time-varying electrical parameter; and
   an imaging controller that receives the respiration characteristic and controls the diagnostic imaging scanner based thereon.

2. The imaging system as set forth in claim 1, wherein the time-varying electrical parameter includes a time-varying resistance, the differentiator computes a first derivative, and the monitor further includes:
   a respiration state processor that computes the respiration parameter as one of:
   inhaling corresponding to a positive time derivative of the time varying resistance,
   exhaling corresponding to a negative time derivative of the time varying resistance, and
   a breath-hold state corresponding to a substantially zero time derivative of the time-varying resistance.

3. A diagnostic imaging system including:
   a diagnostic imaging scanner that acquires imaging data of a subject in an examination region;
   a reconstruction processor that reconstructs the acquired imaging data into an image representation;
   a pair of electrodes adapted to externally contact a thoracic region of the subject;
   an electrical meter that measures a time-varying electrical parameter across the electrode pair by applying a voltage or current pulse train having a frequency substantially higher than the heart rate across the pair of electrodes;
   a monitor that extracts a time-varying respiration characteristic from the measured time-varying electrical parameter, the monitor including a respiratory cycle phase processor that estimates a respiratory cycle phase based on the time varying electrical parameter; and
   an imaging controller that receives the respiration characteristic and controls the diagnostic imaging scanner based thereon.

4. The imaging system as set forth in claim 3, wherein the time-varying electrical parameter is selected from a group consisting of:

a time-varying complex impedance,
a time-varying resistance,
a time-varying capacitance,
time-varying inductance,
a time varying current, and
a time varying voltage.

5. The imaging system as set forth in claim 3, wherein the diagnostic imaging scanner is a computed tomography scanner.

6. The imaging system as set forth in claim 3, wherein the electrical meter includes:
a voltage pulse generator that applies a voltage pulse train to the electrode pair; and
an ammeter that measures an electrical current flowing between the electrode pair responsive to the applied voltage pulse train.

7. The imaging system as set forth in claim 3, wherein the monitor includes:
a calibration that correlates electrical parameter values with a tidal volume of air in lungs of the subject; and
a transform processor that references the calibration to transform the time varying electrical parameter into a time-varying tidal volume of air in the lungs.

8. The imaging system as set forth in claim 3, further including:
an image data binning means for sorting imaging data into respiratory cycle phase bins based on the time-varying respiration characteristic, the reconstruction processor reconstructing data in a selected one or more of the respiratory cycle phase bins.

9. The imaging system as set forth in claim 3, wherein the electrical meter applies the voltage or current pulse train having a frequency in the tens of kilohertz range.

10. A diagnostic imaging system including:
a diagnostic imaging scanner that acquires imaging data of a subject in an examination region;
a reconstruction processor that reconstructs the acquired imaging data into an image representation;
a pair of electrodes adapted to externally contact a thoracic region of the subject;
an electrical meter that measures a time-varying electrical parameter across the electrode pair by applying a voltage or current pulse train having a frequency substantially higher than the heart rate across the pair of electrodes;
a monitor that extracts a time-varying respiration phase characteristic from the measured time-varying electrical parameter;
an electrocardiograph that measures electrocardiographic data of the subject using at least the pair of electrodes; and
an imaging controller that receives the respiration characteristic and controls the diagnostic imaging scanner based thereon.

11. A medical diagnostic imaging method including:
acquiring imaging data of a medical imaging patient;
reconstructing at least a part of the acquired imaging data into an image representation;
externally contacting a thoracic region of the patient with the pair of external electrodes;
measuring a time-varying electrical parameter across the external electrodes pair during the acquiring of imaging data, the measuring including applying one of a voltage and a current to the external electrodes pair, measuring the other of voltage and current responsive to the applying, and computing the time-varying electrical parameter based on the applied and measured quantities;
computing a time-varying respiration characteristic based on the measured time-varying electrical parameter wherein the computing of a time-varying respiration characteristic from the time-varying electrical parameter includes computing a time varying respiratory cycle phase function based on the time-varying electrical parameter; and
adjusting an imaging parameter responsive to the respiration characteristic.

12. The method as set forth in claim 11, wherein the contacting of the thoracic region with the electrodes pair includes:
relatively arranging the electrodes pair with a substantial portion of the thoracic region disposed therebetween.

13. The method as set forth in claim 11, wherein the acquiring of imaging data includes:
passing x-rays through an imaging region;
measuring x-ray intensities after passing through the imaging region; and
computing x-ray absorption data from the measured x-ray intensities.

14. The method as set forth in claim 11, further including:
measuring electrocardiographic data using the external pair of electrodes.

15. The method as set forth in claim 11, wherein the measuring of electrocardiographic data using the pair of electrodes is performed substantially simultaneously with the measuring of a time-varying electrical parameter across the electrodes pair.

16. The method as set forth in claim 11, wherein the measuring of a time-varying electrical parameter across the electrodes pair includes:
measuring a time-varying resistance across the electrodes pair.

17. The method as set forth in claim 11, wherein the computing of a time-varying respiratory cycle phase function based on the time-varying electrical parameter includes:
determining a respiration state based on a temporal slope of the time-varying electrical parameter.

18. The method as set forth in claim 11, wherein the computing of a time-varying respiratory cycle phase function based on the time-varying electrical parameter includes:
selecting a respiration state based on a temporal slope of the time-varying electrical parameter, the respiration state being selected as one of:
inhaling corresponding to a positive temporal slope,
exhaling corresponding to a negative temporal slope, and
a breath-hold state corresponding to a generally horizontal slope.

19. The method as set forth in claim 11, wherein the computing of a time-varying respiration characteristic from the time-varying electrical parameter further includes:
computing a respiration rate proportional to a temporal frequency of the time varying electrical parameter.

20. The method as set forth in claim 11, wherein the computing of a time-varying respiration characteristic from the time-varying electrical parameter further includes:
computing a time-varying tidal volume function of air in lungs of the patient based on the time varying electrical parameter.

21. The method as set forth in claim 11, further including:
gating the acquiring of imaging data based on the extracted time varying respiratory cycle phase function.

22. The method as set forth in claim 11, wherein the applying one of a voltage and a current to the external electrodes pair comprises:
applying a pulse train of voltage or current pulses having a pulse frequency substantially higher than the heart rate to the electrodes pair.

* * * * *